United States Patent [19]

Schraga

[11] Patent Number: 5,395,388
[45] Date of Patent: Mar. 7, 1995

[54] SINGLE UNIT LANCET DEVICE

[76] Inventor: Steven Schraga, 1841 NE. 146 St., North Miami, Fla. 33181

[21] Appl. No.: 151,862

[22] Filed: Nov. 15, 1993

[51] Int. Cl.$^6$ .............................................. A61B 17/32
[52] U.S. Cl. .................................... 606/182; 606/181
[58] Field of Search ............................. 606/181–185, 606/188; 604/136, 156, 157

[56] References Cited

U.S. PATENT DOCUMENTS

| | | | |
|---|---|---|---|
| 3,760,809 | 9/1973 | Campbell, Jr. | 606/182 |
| 4,414,975 | 11/1983 | Ryder et al. | 606/182 |
| 4,535,769 | 8/1985 | Burns | 606/182 |
| 4,539,988 | 9/1985 | Shirley et al. | 606/182 |
| 4,715,374 | 12/1987 | Maggio | 606/182 |
| 4,735,203 | 4/1988 | Ryder et al. | 606/182 |
| 4,892,097 | 1/1990 | Ranalletta et al. | 606/182 |
| 4,983,178 | 1/1991 | Schnell | 606/181 |

*Primary Examiner*—Ralph A. Lewis
*Attorney, Agent, or Firm*—Malloy & Malloy

[57] ABSTRACT

A single use disposable lancet device including a housing wherein a spring is contained, the spring including a first end fixed within the housing and having a movable second end zone with a pointed blade or terminal end, the second end zone being movable relative to a normal position with the pointed terminal end contained within the housing and adjacent a first opening in the housing, between a cocked position completely within the housing and with energy stored in the spring, and a piercing position with the second end zone in the first opening and the pointed terminal end momentarily exterior of the housing. The housing further including a lever arm including a holding tip to maintain the second end zone in cocked position until pivotally moved by an operator resulting in release of the second end zone such that the second end zone moves to its piercing position, and as soon as it pierces, retracts into the housing.

5 Claims, 1 Drawing Sheet

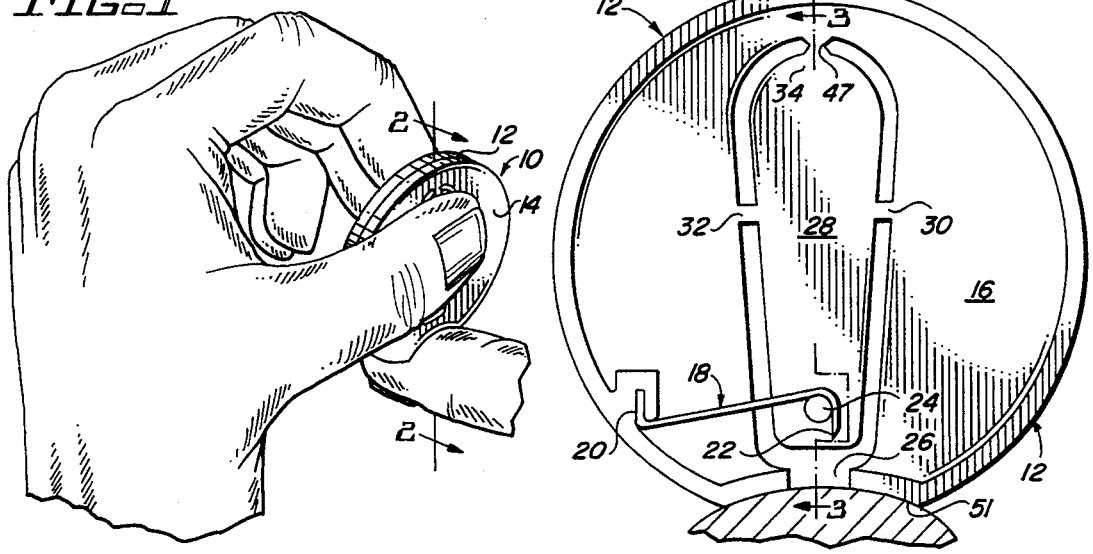
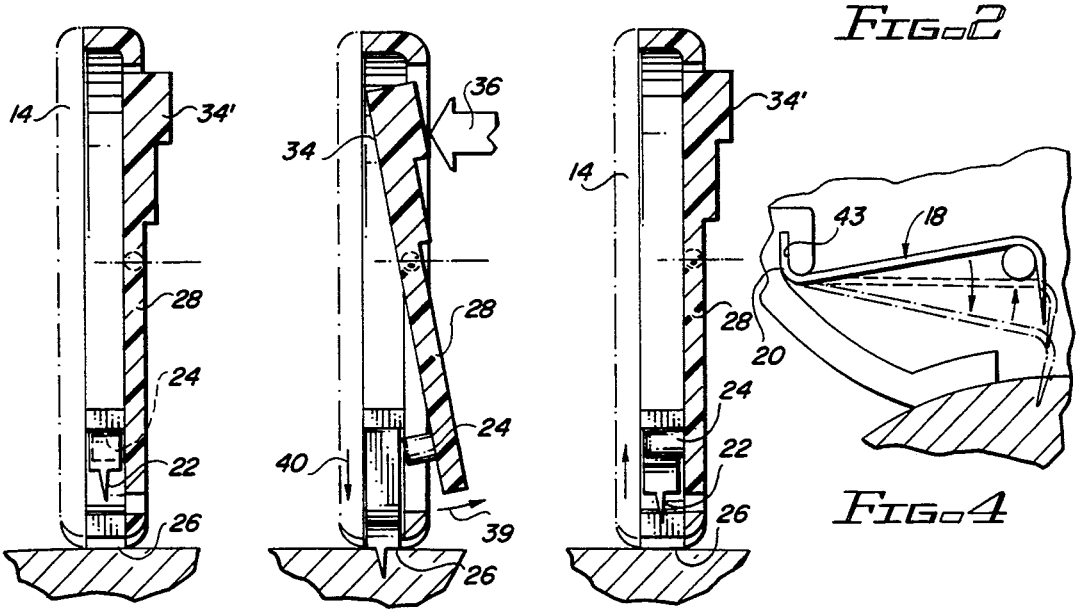
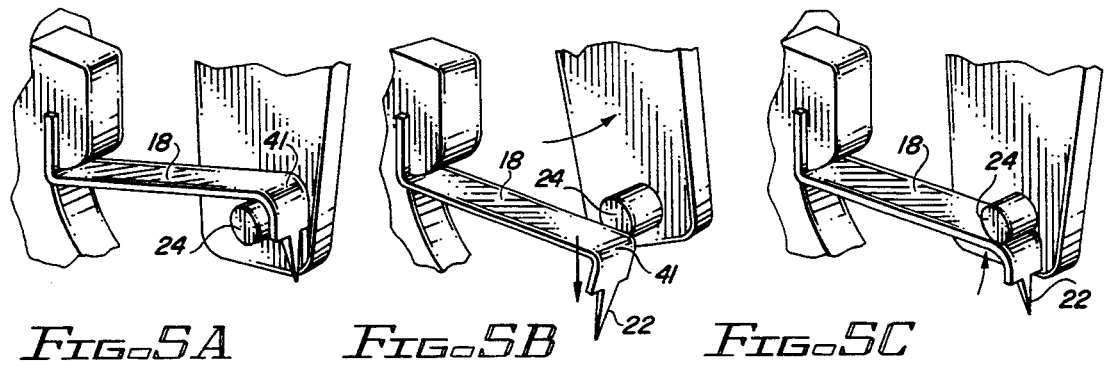

SINGLE UNIT LANCET DEVICE

BACKGROUND OF THE INVENTION

1. Field of the Invention

This invention relates to a lancet device.

2. Summary of the Invention

In the past, there have been many types of lancet devices. Such lancet devices have come to be recognized as somewhat dangerous since blood is involved; and, therefore, there is a need for a single use lancet device, which is of inexpensive construction and which protectively houses the piercing tip of the needle point or blade point within the lancet housing at all times, before and after use. In other words, the sharpened tip of the lancet is outside the housing only during the actual pricking operation.

More particularly, this invention in one embodiment is of a lancet device which has an elongate spring which is sharpened at one end to form a piercing tip, while the other end is captivated within the housing of the lancet. Prior to use, the spring is entirely captivated within the housing in a cocked position and held in that position by a holding pin. The pin is swingable upon pressing a lever arm so that the energy stored in the cocked spring is released and the sharpened tip travels through an opening for the pricking operation and immediately retracts within the housing to its normal, parked position. In other words, the normal, relaxed position of the spring is with the tip protectively within the housing. Prior to use, the spring is in a cocked position. In use, the tip moves from the cocked position to a piercing position but returns immediately to the normal relaxed position with the tip protectively completely within the housing.

It is an object of this invention to provide a simple lancet device of inexpensive construction which includes a spring with a pointed tip end for use in pricking in order to obtain a sample of blood and the tip is at all times protectively within the housing except momentarily when the pricking operation is performed.

BRIEF DESCRIPTION OF THE DRAWINGS

FIG. 1 is a perspective view illustrating the use of the single use disposable lancet device and with the lancet housing being grasped by a user and held in piercing relation to the thumb pad of a patient.

FIG. 2 is a view taken on the plane indicated by the line 2—2 of FIG. 1 and looking in the direction of the arrows and illustrating the interior of the base portion of the housing and a cover portion of the housing, the latter being hingedly connected to the base portion and being partially shown.

FIG. 3A is a view taken on the plane indicated by the line 3—3 of FIG. 2 and looking in the direction of the arrows to illustrate the pointed end of the lancet captivated in a cocked position within the housing.

FIG. 3B is a view in cross section taken on the plane indicate by the line 3—3 of FIG. 2 and looking in the direction of the arrows and illustrating the pointed end of the lancet device in a momentary position of piercing and with arrows indicating the direction of force and movement.

FIG. 3C is a view taken on the plane indicated by the line 3—3 of FIG. 2 and looking in the direction of the arrows and illustrating the lancet spring in a normal, relaxed position, after use.

FIG. 4 is a partial view to illustrate the spring in a cocked position and a) illustrating the direction of movement of the piercing tip when released for momentary movement into piercing engagement with the flesh of a user, shown in dotted lines, and b) a relaxed position with the pointed tip retracted and within the housing, also shown in dotted lines.

FIGS. 5A, 5B, and 5C illustrate the operation of the device with the spring with the pointed end in a cocked position in FIG. 5A; in an extended piercing position shown in FIG. 5B; and in a relaxed position in FIG. 5C with the pointed end within the lancet housing.

DETAILED DESCRIPTION OF THE PREFERRED EMBODIMENT

Use of the single use disposable lancet device is seen in FIG. 1; and it is designated by the numeral 10. In this embodiment, it is composed of a housing having a base portion 12 (also see FIG. 2) and a cover portion 14. The base portion of the housing may be hingedly connected to the cover portion 10, for swinging movement of the cover portion into closing relation of the interior 16 of the housing base portion 12. Within the housing, there is captivated a spring 18 with a first end zone 20 and a pointed second end zone 22. The spring is held in a cocked position by a holding tip means or pin 24 in the housing and in adjacent relation to an opening 26 in the housing. A lever arm 28 is pivotally connected as at 30 and 32 to the base portion. Thus, as seen for example in FIG. 3B, when the operator means on the second end zone 34 of the lever arm 28 is pressed in the direction of the arrowed line 36 in FIG. 3B, the pin 24 will release the end 22 by pivotally tilting in the direction of the arrowed line 39 so that the pointed tip moves downwardly as shown by the arrowed line 40 through the opening 26, moving from the cocked position shown in FIG. 3A to the piercing position shown in FIG. 3B and subsequently to a normal or relaxed position shown in FIG. 3C with the piercing tip protectively within the housing. This operation is also shown in FIG. 4. Further, as illustrated in FIG. 3A, the second end zone 34', in an alternative embodiment, includes a stepped configuration such that when the operator means of the second end zone 34' are utilized, an operator's finger will not penetrate the housing.

In a preferred embodiment, the housing is of one piece molded plastic material and the spring is a flat spring material of elongate form formed with a crotch as at 41 which engages the pin 24 when in the cocked position, see FIG. 5A and FIG. 4. The tip of the spring is pointed and thus there is combined the operation of the spring and the needle point or blade point. The means captivating the spring are seen for example in FIG. 4 wherein a notch 43 is provided to receive the end 20 of the spring. Also in the preferred embodiment, see FIG. 2, there may be a slight interconnection 47 of the end of the lever so that when pressure is applied as in the direction of the arrow 36 in FIG. 3B, this weakened section will break. Thereafter, a user will know that the device has been used. As seen in FIG. 2, a preferred embodiment provides an arcuate recess 51 annularly arranged about the opening 26 to serve as a shield and to cradle the end of the finger or thumb of a user. The recess 51 is also adapted to enable use of the lancet device on an earlobe, heel, or other similar location.

Thus, this invention actually uses the spring as a needle without the need for separate pieces, the spring functioning to push the lancet upward so that the needle tip on the hub pops out of the lancet housing and with the important feature that upon release of the cocked lancet blade or needle, stored energy in it is released such that it travels through the normal position to pierce a user and automatically retracts so that the sharpened tip is completely within the lancet housing and protectively housed therein. In the preferred configuration, the housing is generally disk shaped and about the size of a quarter to a half-dollar size. It is preferred that it be round and the housing may be in two parts which are snapped, glued, hinged, or welded together.

While this invention has been shown in what is considered to be a practical and preferred embodiment, it is recognized that departures may be made within the spirit and scope of this invention which should therefore not be limited except as set forth in the claims which follow and within the doctrine of equivalents.

What is claimed is:

1. A single use disposable lancet device comprising:
   a housing, said housing including a lever arm having a first end zone and a second end zone;
   a holding member connected to said second end zone of said lever arm, said holding member extending within said housing,
   a spring member within said housing, said spring member including a distal end, a proximal end, and a pointed lancet tip at said distal end, said proximal end being operably connected to said housing,
   said housing having an opening sized to permit said pointed tip to project exterior to said housing,
   said spring member being disposed within said housing in an initial pro-tensioned cocked position wherein said distal end is in releasable engagement with said holding member and said spring member is biased for movement into an unstressed position,
   said housing being structured and disposed to protectively shield said pointed tip of said spring member in said cocked position,
   said lever arm being pivotally connected to said housing between said first end zone and said second end zone such that actuation of said first end zone causes said holding member to disengage from said distal end of said spring member,
   said spring member being pivotally movable from said initial pro-tensioned position through said unstressed position to a piercing position wherein said pointed tip momentarily projects exterior of said housing opening, said spring member rebounding from said piercing position and finally coming to rest in said unstressed position,
   said housing being structured and disposed to protectively shield said pointed tip of said spring member in said final unstressed position,
   said housing comprising a means for shielding said spring member from being displaced from said final unstressed position.

2. A lancet device as recited in claim 1 wherein said spring member is of elongate configuration and said pointed tip is integrally formed therewith.

3. A lancet device as recited in claim 1 wherein said lever arm is integrally formed with said housing.

4. A lancet device as recited in claim 1 wherein said first end zone of said lever arm has an outwardly raised configuration.

5. A lancet device as recited in claim 1 wherein said first end zone of said lever arm includes a frangible section connected to said housing in said initial pre-tensioned position, said frangible section being breakable upon actuation of said first end zone so as to indicate that the lancet device has been used.

* * * * *